(12) United States Patent
Mandai et al.

(10) Patent No.: US 6,410,757 B1
(45) Date of Patent: Jun. 25, 2002

(54) BACCATIN DERIVATIVES AND A PROCESS FOR PRODUCING THE SAME

(75) Inventors: Tadakatsu Mandai, 1174-371, Tsurajima, Tsurajima-cho, Kurashiki-shi, Okayama-ken; Hiroshi Okumoto, Okayama-ken; Katsuyoshi Nakanishi, Yokohama; Koji Hara, Yokohama; Katsuhiko Mikuni, Yokohama; Kozo Hara, Yokohama, all of (JP)

(73) Assignees: Bio Research Corporation of Yokohama; Ensuiko Sugar Refining Co. Ltd., both of Yokohama; Tadakatsu Mandai, Kurashiki, all of (JP)

( * ) Notice: Subject to any disclaimer, the term of this patent is extended or adjusted under 35 U.S.C. 154(b) by 0 days.

(21) Appl. No.: 09/499,393

(22) Filed: Feb. 7, 2000

(30) Foreign Application Priority Data

Feb. 16, 1999 (JP) ............................................. 11-037055
Aug. 2, 1999 (JP) ........................................... 11-218730

(51) Int. Cl.$^7$ ............................................. C07D 305/14
(52) U.S. Cl. ........................................ 549/510; 549/511
(58) Field of Search ................................. 549/510, 511

(56) References Cited

U.S. PATENT DOCUMENTS 6,136,990 A    10/2000  Mandai et al. ............... 549/510

FOREIGN PATENT DOCUMENTS

EP    0 617 034    9/1994

*Primary Examiner*—Ba K. Trinh
(74) *Attorney, Agent, or Firm*—Oblon, Spivak, McClelland, Maier & Neustadt, P.C.

(57) ABSTRACT

The object of the invention is to develop baccatin derivatives useful for preparing taxoid compounds such as paclitaxel and a process for the producing the same. The invention provides baccatin derivatives represented by the general formula (I) as well as a process for producing baccatin derivatives represented by the general formula (I) above, which comprises allowing a baccatin represented by the general formula (II) to react with a β-ketoester in the absence of a catalyst or in the presence of a tin compound or an amine base, preferably under reduced pressure.

20 Claims, No Drawings

BACCATIN DERIVATIVES AND A PROCESS FOR PRODUCING THE SAME

FIELD OF THE INVENTION

The present invention relates to a baccatin derivative and a process for producing the same, and in particular to a baccatin derivative of the general formula (I) comprising β-ketoester bound to a baccatin whose hydroxyl groups at the 7- and 10-positions are protected, as well as a process for producing the same. This material is useful for preparing taxoid compounds such as paclitaxel.

BACKGROUND OF THE INVENTION

Paclitaxel (trade name: Taxol) is one kind of anticancer agent taken from a *Taxus brevifolia* (yew tree) and it is known to be effective particularly against breast cancer and lung cancer. However, the amount of paclitaxel taken from the *Taxus brevifolia* is very small, and the problem of destruction of forests is caused by stripping the bark from the tree.

On the other hand, 10-deacetylbaccatin III can be taken again because this compound is obtained from leaves of the tree and it is useful as a precursor of paclitaxel or its derivative docetaxel (trade name: Taxotere).

For synthesis of the taxoid compounds, semi-synthetic methods are known, and the following methods have been reported: (a) a method by using β-lactam (European Patent No. 0400971), (b) a method by using an oxazoline compound (International Patent Kokai No. 504444/1995), (c) a method by using a thioester compound (International Patent Kokai No. 505360/1998), and (d) a method by using cinnamic acid (Tetrahedron, Vol. 42, p. 4451 (1986)). These methods are related to the esterification for binding a carboxylic acid compound to an unprotected hydroxyl group at the 13-position in baccatin, or to the esterification using an activated carboxylic acid (thioester).

In general, the preparation of ester compounds can be accomplished by a method of binding a carboxylic acid compound to an alcohol compound with a condensation agent such as dicyclohexylcarbodiimide or diisopropylcarbodiimide in the presence of abase such as pyridine or 4-dimethylaminopyridine; by a method of using an acid anhydride/acid halide; or by transesterification using an acid catalyst etc. For example, the transesterification using an ester compound and an alcohol compound is known as a general method as described in publications such as Chemical Review, Vol. 93, p. 1449 (1993) and Journal of Organic Chemistry, Vol. 50, p. 3618 (1985).

Up to now, the reaction of introducing a side-chain moiety onto a hydroxyl group at the 13-position is limited to the method of binding an carboxylic acid and an activated carboxylic acid (thioester) to the hydroxyl group as described above, and there has been no report on a method of introducing an ester compound as a precursor of a side-chain moiety into the hydroxyl group at the 13-position by transesterification. By introducing an ester compound as a precursor of a side-chain moiety, a compound having a different functional group to that of the conventional side-chain moiety can be easily prepared, and the possibility of obtaining a compound having a different physiological activity than ever before is suggested. In general, the transesterification is conducted in the presence of an acid catalyst such as sulfuric acid or p-toluenesulfonic acid, an amine base such as 4-dimethylaminopyridine or 1,8-diazabicyclo[5,4,0]undecene, or titanium tetraalkoxide etc., but even the transesterification where the reaction proceeds between alcohol and ester is also reported in e.g. Journal of the American Chemical Society, p. 4195 (1951).

SUMMARY OF THE INVENTION

In view of the circumstances described above, the inventors have extensively studied a method of introducing a side-chain moiety precursor by transesterification and attempted to develop a baccatin derivative having β-ketoester bound via an ester linkage to a hydroxyl group at the 13-position in baccatin and a process for producing the same.

As a result, the inventors have found that when β-ketoester is allowed to react with a baccatin in the presence of either a tin compound or an amine base preferably under reduced pressure, the β-ketoester is bound via an ester linkage to the baccatin by transesterification, and the present invention was thereby completed.

Further, the inventors have extensively studied a method of introducing a side-chain moiety precursor by transesterification in the absence of a catalyst and attempted to develop a baccatin derivative having a β-ketoester bound via an ester linkage to a hydroxyl group at the 13-position in baccatin, as well as a process for producing the same.

The present invention has the following aspects and embodiments:

(1) The first aspect of the present invention relates to a baccatin derivative represented by the general formula (I):

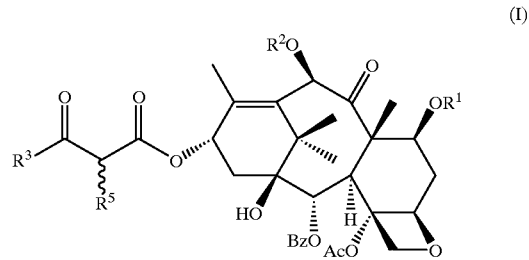

(wherein $R^1$ and $R^2$ simultaneously or independently represent a hydroxyl-protecting group, $R^3$ represents any one group selected from the group of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group and a thienyl group, $R^5$ represents a hydrogen atom or an alkyl group, Bz represents abenzoyl group, and Ac represents an acetyl group).

(2) The second aspect of the present invention relates to a process for producing a baccatin derivative represented by the general formula (I) described above, which comprises allowing a baccatin to react with a β-ketoester in the presence of a tin compound or an amine base, wherein the baccatin is represented by the general formula (II):

(II)

(wherein R[1] and R[2] simultaneously or independently represent a hydroxyl-protecting group, Bz represents a benzoyl group, and Ac represents an acetyl group).
(3) As the third aspect of the present invention, in (2) above, the reaction is conducted under reduced pressure.
(4) The forth aspect of the present invention also relates to a process for producing a baccatin derivative represented by the general formula (I) above, which comprises allowing a baccatin represented by the general formula (II) to react with a β-ketoester in the absence of a catalyst:

(II)

(wherein Rand R[2] simultaneously or independently represent a hydroxyl-protecting group, Bz represents a benzoyl group, and Ac represents an acetyl group).
(5) As the fifth aspect of the present invention, in (4) above, the reaction is conducted under reduced pressure.
(6) The sixth aspect of the present invention further relates to a baccatin derivative represented by the general formula (III):

(III)

(wherein R[1] and R[2] simultaneously or independently represent a hydroxyl-protecting group, n is an integer of 1 to 5, Bz represents a benzoyl group, and Ac represents an acetyl group)
(7) The seventh aspect of the present invention relates to use of a baccatin derivative represented by the general formula (I) described in (1) above or a baccatin derivative represented by the general formula (III) described in (6) above for producing taxoid compounds such as paclitaxel.

DETAILED DESCRIPTION OF THE INVENTION

Hereinafter, the present invention is described in detail.

The baccatin used in the present invention can be 10-deacetylbaccatin III extracted from yew trees, a compound analogous thereto, or a compound obtained by synthesis from a low-molecular compound. In particular, 10-deacetylbaccatin III is suitable for efficiently achieving the present invention.

10-Deacetylbaccatin III used in the present invention, to which a protecting group was introduced, is represented by the general formula (II) above.

The hydroxyl-protecting group in the above formula includes protecting groups described in e.g. "New Course of Experimental Chemistry, 14, Organic Synthesis V, Chapter 11-1, compiled by the Chemical Society of Japan". Specific protecting groups include triethylsilyl group, benzyloxycarbonyl group, acetyl group, allyloxycarbonyl group etc.

Then the β-ketoester used in the present invention is represented by any of the following formulae:

(wherein R[3] is a group selected from an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group and a thienyl group, preferably a phenyl group, p-methoxyphenyl group, 2-furyl group, o-trifluoromethyl phenyl group, m-fluorophenyl group and cyclohexyl group. R[4] is a nucleus of alcohol for forming an ester with a carboxyl group and includes a methyl group, ethyl group, isopropyl group and allyl group);

(wherein, R[3] is a group selected from an unsubstituted or substituted phenyl group, an unsubstituted or substituted furyl group, an unsubstituted or substituted pyridinyl group, analkyl group, ahydroxyalkyl group, ahalogenatedalkyl group, a cyclic alkyl group and a thienyl group. Specifically, as R[3] may be mentioned a phenyl group, p-methoxyphenyl group, 2-furyl group, o-trifluoromethylphenyl group, m-fluorophenyl group or cyclohexyl group. R[4] is a nucleus of alcohol forming an ester with a carboxyl group and includes a methyl group, ethyl group, isopropyl group and allyl group. R[5] is a hydrogen atom or an alkyl group, examples of the alkyl group include a methyl group, ethyl group etc.);

(wherein, R[4] is a nucleus of alcohol forming an ester with a carboxyl group, and specific examples include methyl group, ethyl group, isopropyl group and allyl group. Further, n is an integer of 1 to 5).

The β-ketoester may be used a commercial product, or it can be prepared by reacting an acid chloride with methyl acetoacetate. The acid chloride in this case is obtained by a general reaction of carboxylic acid with oxalyl chloride. Specific examples of the carboxylic acid include methoxybenzoic acid, monofluorobenzoic acid, hydroxybenzoic acid, trifluoromethylbenzoic acid.

The β-ketoester used in the present invention includes e.g. methyl p-methoxybenzoylacetate, methyl o-trifluoromethylbenzoylacetate, methyl m-trifluoromethylbenzoylacetate, methyl p-trifluoromethylbenzoylacetate, methyl o-fluorobenzoylacetate, methyl m-fluorobenzoylacetate, methyl 2-furanoylacetate, methyl cyclohexanoylacetate, methyl 2-oxocyclopentylacetate, methyl 2-methylbenzoylacetate etc.

The reaction of baccatin with β-ketoester can be conducted by using excess amount of β-ketoester (5 to 30 equivalents) without adding other solvent. However, the reaction can also be conducted in the presence of other solvent optionally, and such solvent includes solvent having high boiling point such as diethylene glycol dimethyl ether, triethylene glycol dimethyl ether and cymene.

The process of the second aspect of the present invention is conducted in the presence of a tin compound or an amine base. Even if a titanium compound which is generally used in transesterification, such as tetraisopropyl titanate other than the compound described above, the desired compound can be obtained even though the yield is low and a large amount of byproducts are produced. The tin compound includes 1-chloro-3-hydroxy-tetrabutyldistannoxane, 1,3-dichlorotetrabutyldistannoxane etc., and the amine base includes 4-dimethylaminopyridine (DMAP), 4-pyrrolidinopyridine, N,N-dimethylaniline, 1,8-diazabicyclo[5,4,0]-7-undecene (DBU), tri-n-octylamine etc. The reaction may be conducted by adding the tin compound in an amount of 2%, based on baccatin, and the amine base in an amount up to 2 equivalents, based on baccatin.

In addition, the process of the forth aspect of the present invention may also be conducted in the absence of a catalyst used in general transesterification.

Further, the reaction of baccatin with β-ketoester can also be conducted at normal pressure, but this results in a long reaction time, so the reaction is conducted preferably at a reduced pressure of 0.5 to 400 mmHg using a vacuum device such as aspirator and vacuum pump. In particular, preferred conditions are 0.5 to 1 mmHg when the reaction is conducted in the absence of a solvent or 20 to 40 mmHg when a solvent is added. The reaction is conducted at 60 to 120° C., preferably 90° C., for 1.5 to 24 hours, preferably 2.5 to 5 hours.

An excess amount of β-ketoester is recovered by trapping it in the line for reducing pressure and can be utilized again.

Hereinafter, the present invention is described specifically by reference to a typical example in which the baccatin used is 10-deacetylbaccatin III.

10-Deacetylbaccatin III wherein hydroxyl groups at 7- and 10-positions have been protected can be produced by the following reaction scheme I:

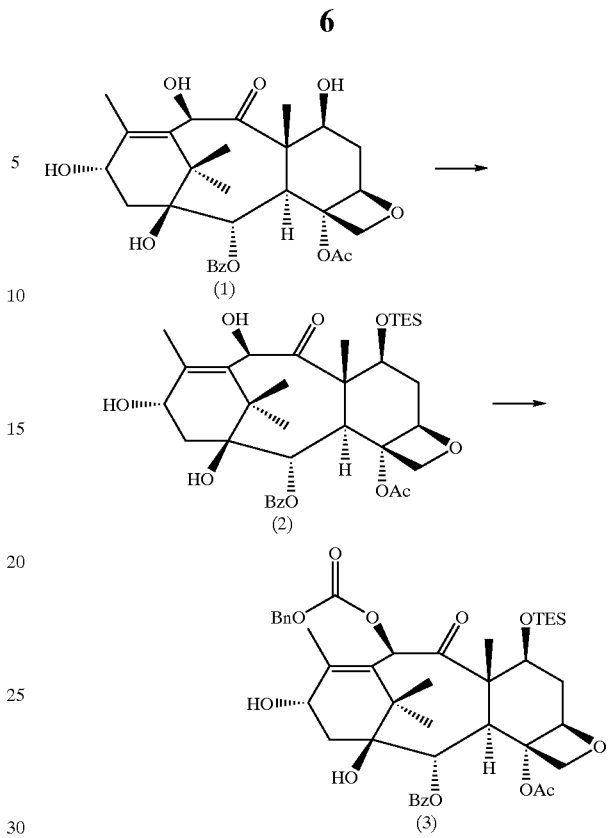

Triethylsilyl chloride, imidazole and dichloromethane are added to 10-deacetylbaccatin III (Compound (1)), and the mixture is reacted at 0 to 100° C., preferably 20° C., for 0.5 to 100 hours, preferably 3 hours, to give Compound (2) wherein a hydroxyl group at the 7-position has been protected.

Benzyloxycarbonyl chloride, 4-dimethylaminopyridine and dichloromethane are added to said compound (2), and the mixture is reacted at −20° C. to 30° C., preferably 0° C., for 0.5 to 100 hours, preferably 14 hours, to give Compound (3) wherein a benzyloxycarbonyl group has been introduced at the 10-position.

The compound of the general formula (I) having β-ketoester introduced by transesterification into a hydroxyl group at the 13-position in 10-deacetylbaccatin III having protected hydroxyl groups at the 7- to 10-positions, can be produced by the following reaction scheme II:

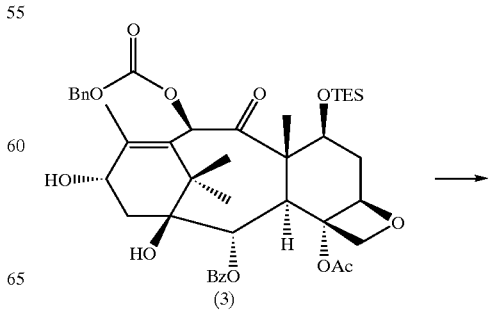

-continued

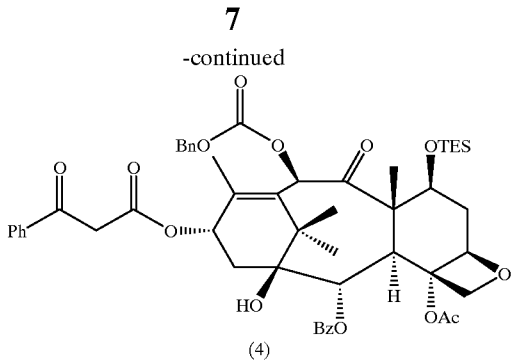

(4)

The β-ketoester and, if necessary, a tin compound or an amine base as a catalyst are added to Compound (3), that is, 10-deacetylbaccatin III wherein hydroxyl groups at the 7- and 10-positions have been protected, and the mixture is reacted under reduced pressure at 80 to 120° C., preferably 90° C., for 1.5 to 24 hours, preferably 5 hours, whereby an ester compound (Compound (4)) is obtained.

Taxoid compounds can be prepared via several steps from the baccatin derivative obtained in the present invention as the starting material.

As the resulting taxoid derivatives besides paclitaxel and docetaxel, it is possible to obtain compounds having a non-phenyl functional group as the side chain at the 3'-position; compounds having a functional group other than a benzoyl group or t-butoxycarbonyl group on an amino group at the 3'-position; and compounds having various acyl groups bound to hydroxyl groups at the 7- and 10-positions, and it can be expected that compounds having antitumor activity, which is different from that of compounds known so far are, obtained.

As described in detail hereinbefore, the present invention provides a baccacin derivative by binding β-ketoester via an ester linkage to a hydroxyl group at the 13-position in baccatin such as 10-deacetylbaccatin III through transesterification therebetween in the absence of a catalyst or in the presence of a tin compound or an amine base, preferably under reduced pressure, as well as a process for producing the same.

Further, the baccatin derivatives of the present invention are useful as starting materials for preparing taxoid compounds such as paclitaxel as an anticancer agent.

EXAMPLES

Hereinafter, the present invention is described in more detail, which however are not intended to limit the present invention.

Production Example 1

Production of β-ketoester 5.4 ml of methyl acetoacetate was added to 4.4 g of sodium hydride dispersed in 100 ml of tetrahydrofuran at 0° C. After 30 minutes, 9.4 g of p-methoxybenzoyl chloride dissolved in 10 ml of tetrahydrofuran was added thereto at the same temperature of 0° C., and the mixture was then stirred for 3 hours. Aqueous saturated ammonium chloride and methanol were added to the reaction solution which was then extracted and purified whereby the desired β-ketoester was obtained.

This compound was dissolved in chloroform-d and analyzed by $^1$H-NMR, and its structure was determined by assignment of each peak, and it was thus confirmed that the product was the β-ketoester represented by the following structural formula:

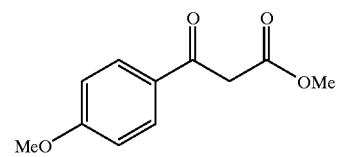

$^1$H-NMR (500 MHz, CDCl$_3$) of methyl p-methoxybenzoylacetate 3.75 (0.95H*3, s), 3.79 (0.05H*3, s), 3.85 (0.05H*3, s), 3.88 (0.95H*3, s), 3.96 (0.95H*2, s), 6.90–7.00 (2H, m), 7.72–7.78 (0.05H*2, m), 7.90–7.99 (0.95H*2, m), 12.55 (0.05H, s).

Example 1

Production of 7-Triethylsilyl-10-benzyloxycarbonyl-13-(3-phenyl-3-keto-propanoyl)-10-deacetylbaccatin III 6.9 ml of ethyl benzoylacetate and 11 mg of 1-chloro-3-hydroxy-tetrabutyldistannoxane were added to 1.586 g of compound (Compound (3), C$_{43}$H$_{56}$O$_{12}$Si, a molecular weight of 792.99), that is, 10-deacetylbaccatin III (1) wherein a hydroxyl group at the 7-position was protected with a triethylsilyl group and a hydroxyl group at the 10-position was protected with a benzyloxycarbonyl group by the conventional method, and the mixture was reacted at 90° C. under reduced pressure (0.5 mmHg) for 3 hours, and excess ethyl benzoylacetate was distilled away in a Kugel Rohr distillation device.

The residue was purified by a silica gel column to give 1.901 g of ester compound (Compound (4), C$_{52}$H$_{62}$O$_{14}$Si, a molecular weight of 939.14).

This compound was dissolved in chloroform-d and analyzed by $^1$H-NMR, and its structure was determined by assignment of each peak, and it was thus confirmed that the product was represented by the structural formula shown as the compound (4) in the reaction scheme II.

$^1$H-NMR (500 MHz, CDCl$_3$) of the ester compound; σ(ppm); 12.51 (0.30H, s), 8.03–8.12 (2H, m), 7.95–8.03 (0.70H*2, m), 7.78–7.85 (0.30H*2, m), 7.30–7.68 (11H, m), 6.32 (0.30H, s), 6.27 (0.70H, s), 6.19–6.30 (1H, m), 5.75 (0.30H, s), 5.63–5.72 (1H, m), 5.17, 5.24 (0.30H*2, ABq, J=12.2 Hz), 5.16–5.22 (0.70H*2, ABq, J=12.2 Hz), 4.97 (0.30H, bd, J=8.3 Hz), 4.92 (0.70H, bd, J=7.9 Hz), 4.50 (0.30H, dd, J=10.4, 6.7 Hz), 4.45 (0.70H, dd, J=10.7, 6.7 Hz), 4.26–4.33 (1H, m), 4.09–4.20 (1H+0.70H*2, m), 3.84 (0.30H, d, J=6.7 Hz), 3.79 (0.70H, d, J=7.0 Hz), 2.48–2.59 (1H, m), 2.20–2.44 (2H, m), 2.37 (0.30H*3, s), 2.23 (0.70H*3, s), 2.14 (0.30H*3, d, J=0.9 Hz), 2.01 (0.70H*3, d, J=0.9 Hz), 1.85–1.95 (1H, m), 1.71 (0.30H*3, s), 1.69 (0.70H*3, s), 1.22 (0.30H*3, s), 1.20 (0.70H*3, s), 1.19 (0.30H*3, s), 1.17 (0.70H*3, s), 0.86–0.95 (9H, m), 0.52–0.63 (6H, m).

Example 2

The reaction was conducted in the same manner as in Example 1 except that 1,3-dichlorotetrabutyldistannoxane was used as the tin compound.

1.03 ml of ethyl benzoylacetate and 3 mg of 1,3-dichlorotetrabutyldistannoxane were added to 238 mg of Compound (3) in Example 1 and allowed to react at 9020 C. under reduced pressure (0.5 mmHg) for 3 hours, and excess ethyl benzoylacetate was distilled away in a Kugel Rohr distillation device.

The residue was purified by a silica gel column to give 252 mg of ester compound (Compound (4), $C_{52}H_{62}O_{14}Si$, a molecular weight of 939.14). Analysis by $^1H$-NMR also indicated that this compound is identical to the compound obtained in Example 1.

Example 3

Compound (4) was produced by using 4-dimethylaminopyridine (DMAP) as the amine base in place of 1-chloro-3-hydroxy-tetrabutyldistannoxane in Example 1.

1.72 ml of ethyl benzoylacetate and 61 mg of 4-dimethylaminopyridine (DMAP) were added to 396 mg of Compound (3) in Example 1, and the mixture was reacted at 90° C. under reduced pressure (0.5 mmHg) for 5.5 hours, and the reaction solution was then poured into 1 N aqueous hydrochloric acid and extracted with ethyl acetate. The organic phase was washed with aqueous saturated sodium hydrogencarbonate, concentrated and purified by a silica gel column to give 449 mg of ester compound (Compound (4), $C_{52}H_{62}O_{14}Si$, a molecular weight of 939.14). Analysis by $^1H$-NMR also indicated that this compound is identical to the compound obtained in Example 1.

Examples 4 and 5

Abenzyloxycarbonyl group was present at the 10-position of baccatin in Example 3, but in this example it is shown that the same reaction can be conducted even with an acetyl group or allyloxycarbonyl group at that position.

1.03 ml of ethyl benzoylacetate and 36 mg of 4-dimethylaminopyridine (DMAP) were added to baccatin (0.3 mmol) protected at the 7-position with a triethylsilyl group and at the 10-position with an acetyl group or an allyloxycarbonyl group, and the mixture was reacted at 90° C. under reduced pressure (0.5 mmHg) for 3 hours, and the reaction solution was poured into 1 N aqueous hydrochloric acid and extracted with ethyl acetate. The organic phase was washed with aqueous saturated sodium hydrogencarbonate, concentrated and purified by a silica gel column to give the ester compound. The measurement results on yield, $^1H$-NMR etc. are described below.

Example 4

Baccatin Wherein a Protecting Group at the 10-Position is an Acetyl Group is used Yield: 231 mg, Recovery: 90.9%; $^1H$-NMR (500 MHz, $CDCl_3$) of the ester compound represented by the following structural formula:

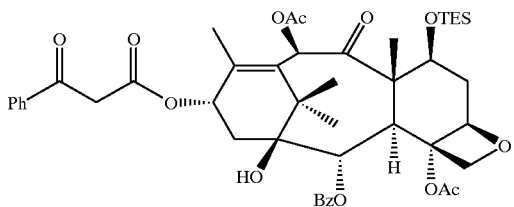

σ(ppm); 12.51 (0.4H, s), 8.08 (2H, d, J=8.2 Hz), 7.96–8.02 (0.6H*2, m), 7.79–7.83 (0.4H*2, m), 7.43–7.68 (6H, m), 6.49 (0.4H, s), 6.44 (0.6H, s), 6.18–6.30 (1H, m), 5.75 (0.4H, s), 5.63–5.72 (1H, m), 4.98 (0.4H, d, J=7.9 Hz), 4.93 (0.6H, d, J=7.9 Hz), 4.51 (0.4H, dd, J=6.7, 10.7 Hz), 4.46 (0.6H, dd, J=6.7, 10.6 Hz), 4.26–4.33 (1H, m), 4.09–4.20 (1H+0.6H*2, m), 3.87 (0.4H, d, J=7.0 Hz), 3.82 (0.6H, d, J=7.1 Hz), 2.47–2.60 (1H, m), 2.15–2.43 (2H, m), 2.37 (0.4H*3, s), 2.23 (0.6H*3, s), 2.19 (0.4H*3, s), 2.17 (0.6H*3, s), 2.12 (0.4H*3, d, J=0.9 Hz), 1.99 (0.6H*3, d, J=0.9 Hz), 1.70 (0.4H*3, s), 1.68 (0.6H*3, s), 1.25 (0.4H*3, s), 1.22 (0.6H*3, s), 1.20 (0.4H*3, s), 1.18 (0.6H*3, s), 0.88–0.98 (9H, m), 0.53–0.65 (6H, m)

Example 5

Baccatin Wherein a Protecting Group at the 10-Position is an Allyloxycarbonyl Group is used Yield: 257 mg, Recovery: 96.3%; $^1H$-NMR (500 MHz, $CDCl_3$) of the ester compound represented by the following structural formula:

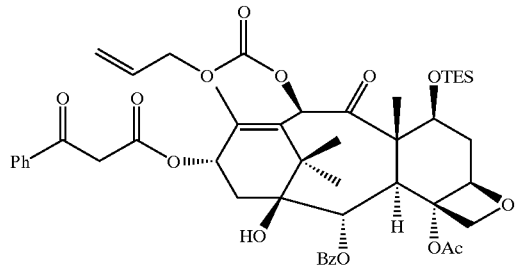

σ(ppm); 12.51 (0.3H, s), 8.03–8.12 (2H, m), 7.94–8.03 (0.7H*2, m), 7.77–7.85 (0.3H*2, m), 7.44–7.70 (6H, m), 6.31 (0.3H, s), 6.18–6.31 (1H, m), 6.25 (0.7H, s), 5.90–6.01 (1H, m), 5.75 (0.3H, s), 5.65–5.71 (1H, m), 5.35–5.42 (1H, m), 5.24–5.32 (1H, m), 4.98 (0.3H, d, J=6.3 Hz), 4.92 (0.7H, d, J=6.2 Hz), 4.59–4.72 (2H, m), 4.50 (0.3H, dd, J=6.7, 10.7 Hz), 4.45 (0.7H, dd, J=6.7, 10.4 Hz), 4.26–4.34 (1H, m), 4.09–4.20 (1H+0.7H*2, m), 3.84 (0.3H, d, J=7.1 Hz), 3.79 (0.7H, d, J=7.0 Hz), 2.48–2.58 (1H, m), 2.20–2.44 (2H, m), 2.37 (0.3H*3, s), 2.24 (0.7H*3, s), 2.13 (0.3H*3, bs), 2.00 (0.7H*3, bs), 1.86–1.95 (1H, m), 1.71 (0.3H*3, s), 1.69 (0.7H*3, s), 1.24 (0.3H*3, bs), 1.22 (0.7H*3, bs), 1.21 (0.3H*3, s), 1.20 (0.7H*3, s), 0.88–0.98 (9H, m), 0.54–0.64 (6H, m).

Example 6

The reaction was conducted in the same manner as in Example 3 except that 4-pyrrolidinopyridine was used as the amine base.

343 μl of ethyl benzoylacetate and 15 mg of 4-pyrrolidinopyridine were added to 79 mg of Compound (3) in Example 1, and the mixture was reacted at 90° C. under reduced pressure (0.5 mmHg) for 3 hours, and the reaction solution was poured into 1 N aqueous hydrochloric acid and extracted with ethyl acetate. The organic phase was washed with aqueous saturated sodium hydrogencarbonate, concentrated and purified by a silica gel column to give 82 mg of ester compound (Compound (4), $C_{52}H_{62}O_{14}Si$, a molecular weight of 939.14).

Example 7

The reaction was conducted in the same manner as in Example 3 except that N,N-dimethylaniline was used as the amine base.

343 μl of ethyl benzoylacetate and 13 μl of N,N-dimethylaniline were added to 79 mg of Compound (3) in Example 1, and the mixture was reacted at 90° C. under reduced pressure (0.5 mmHg) for 2.5 hours, and the reaction solution was poured into 1 N aqueous hydrochloric acid and extracted with ethyl acetate. The organic phase was washed with aqueous saturated sodium hydrogencarbonate, concentrated and purified by a silica gel column to give 84 mg of ester compound (Compound (4), $C_{52}H_{62}O_{14}Si$, a molecular weight of 939.14).

Example 8

The reaction was conducted in the same manner as in Example 3 except that tri-n-octylamine was used as the amine base.

343 μl of ethyl benzoylacetate and 44 μl of tri-n-octylamine were added to 79 mg of Compound (3) in Example 1, and the mixture was reacted at 90° C. under reduced pressure (0.5 mmHg) for 2.5 hours, and the reaction solution was poured into 1 N aqueous hydrochloric acid and extracted with ethyl acetate. The organic phase was washed with aqueous saturated sodium hydrogencarbonate, concentrated and purified by a silica gel column to give 102 mg of ester compound (Compound (4), $C_{52}H_{62}O_{14}Si$, a molecular weight of 939.14).

Example 9

The reaction was conducted in the same manner as in Example 3 except that 1,8-diazabicyclo[5,4,0]-7-undecene (DBU) was used as the amine base.

343 μl of ethyl benzoylacetate and 15 μl of DBU were added to 79 mg of Compound (3) in Example 1, and the mixture was reacted at 90° C. under reduced pressure (0.5 mmHg) for 2.5 hours, and the reaction solution was poured into 1 N aqueous hydrochloric acid and extracted with ethyl acetate. The organic phase was washed with aqueous saturated sodium hydrogencarbonate, concentrated and purified by a silica gel column to give 82 mg of ester compound (Compound (4), $C_{52}H_{62}O_{14}Si$, a molecular weight of 939.14).

Example 10

The reaction was conducted in the same manner as in Example 3 except that imidazole was used as the amine base.

343 μl of ethyl benzoylacetate and 7 mg of imidazole were added to 79 mg of Compound (3) in Example 1, and the mixture was reacted at 90° C. under reduced pressure (0.5 mmHg) for 3 hours, and the reaction solution was poured into 1 N aqueous hydrochloric acid and extracted with ethyl acetate. The organic phase was washed with aqueous saturated sodium hydrogencarbonate, concentrated and purified by a silica gel column to give 76 mg of ester compound (Compound (4), $C_{52}H_{62}O_{14}Si$, a molecular weight of 939.14).

Example 11

No solvent was used in the reaction in Example 1, but diethylene glycol dimethyl ether was used as the solvent in the reaction in this example.

430 μl of ethyl benzoylacetate, 5 mg of the same tin compound as used in Example 1, and 2 ml of diethylene glycol dimethyl ether were added to 396 mg of Compound (3) in Example 1, and the mixture was reacted at 90° C. under reduced pressure (0.5 to 1 mmHg) for 15 hours, and excess ethyl benzoylacetate was distilled away in a Kugel Rohr distillation device. The residue was purified by a silica gel column to give 434 mg of ester compound (Compound (4), $C_{52}H_{62}O_{14}Si$, a molecular weight of 939.14).

Example 12

The reaction was conducted using p-cymene as the solvent.

430 μl of ethyl benzoylacetate, 5 mg of the same tin compound as in Example 1, and 2 ml of p-cymene were added to 396 mg of Compound (3) in Example 1, and the mixture was reacted at 90° C. under reduced pressure (30 to 40 mmHg) for 11 hours, and excess ethyl benzoylacetate was distilled away in a Kugel Rohr distillation device. The residue was purified by asilica gel column to give 460 mg of ester compound (Compound (4), $C_{52}H_{62}O_{14}Si$, a molecular weight of 939.14).

Example 13

The reaction was conducted using triethylene glycol dimethyl ether as the solvent.

430 μl of ethyl benzoylacetate, 61 mg of 4-dimethylaminopyridine (DMAP) and 0.2 ml of triethylene glycol dimethyl ether were added to 396 mg of Compound (3) in Example 1, and the mixture was reacted at 90° C. under reduced pressure (30 to 40 mmHg) for 5 hours, and the reaction solution was poured into 1 N aqueous hydrochloric acid and extracted with ethyl acetate. The organic phase was washed with aqueous saturated sodium hydrogencarbonate, concentrated and purified by a silica gel column to give 417 mg of ester compound (Compound (4), $C_{52}H_{62}O_{14}Si$, a molecular weight of 939.14).

$^1$H-NMR indicated that the compounds obtained in Examples 6 to 13 are identical with the compound obtained in Example 1.

Examples 14 to 20

The desired compound was produced by using various β-ketoesters other than ethyl benzoylacetate as the β-ketoester. Hereinafter, yield etc. are shown when various β-ketoesters were used.

βketoesters (5 equivalents relative to Compound (3)), 61 mg of 4-dimethylaminopyridine (DMAP) and 0.2 ml of triethylene glycol dimethyl ether were added to 396 mg of Compound (3) in Example 1, and the mixture was reacted at 90° C. under reduced pressure (30 to 40 mmHg) for 5 hours whereby various baccatin derivatives were obtained. The yield, $^1$H-NMR etc. are described below.

Example 14

Methyl P-methoxybenzoylacetate

Yield: 379 mg, Recovery: 78.1%; $^1$H-NMR (500 MHz, CDCl$_3$) of the ester compound represented by the following structural formula:

σ(ppm); 12.56 (0.2H, s), 8.03–8.12 (2H, m), 7.93–8.00 (0.8H*2, m), 7.75–7.79 (0.2H*2, m), 7.57–7.64 (1H, m), 7.14–7.52 (7H, m), 6.95–7.02 (2H, m), 6.32 (0.2H, s), 6.27

(0.8H, s), 6.17–6.30 (1H, m), 5.62–5.70 (1H, m), 5.17, 5.24 (0.2H*2, ABq, J=12.2 Hz), 5.14, 5.23 (0.8H*2, ABq, J=12.2 Hz), 4.98 (0.2H, bd, J=9.8 Hz), 4.92 (0.8H, bd, J=7.9 Hz), 4.50 (0.2H, dd, J=10.4, 6.7 Hz), 4.45 (0.8H, dd, J=10.7, 6.7 Hz), 4.26–4.33 (1H, m), 4.13–4.20 (1H, m), 4.06, 4.11 (0.8H*2, ABq, J=15.2 Hz), 3.90 (0.8H*3, s), 3.88 (0.2H*3, s), 3.84 (0.2H, d, J=6.7 Hz), 3.79 (0.8H, d, J=6.7 Hz), 2.48–2.58 (1H, m), 2.37 (0.2H*3, s), 2.25 (0.8H*3, s), 2.13 (0.2H*3, d, J=1.2 Hz), 2.02 (0.8H*3, d, J=1.2 Hz), 1.85–1.94 (1H, m), 1.71 (0.2H*3, s), 1.69 (0.8H*3, s), 1.22 (0.2H*3, s), 1.18–1.22 (1H, m), 1.17 (0.8H*3, s), 0.86–0.97 (9H, m), 0.52–0.63 (6H, m).

Example 15

Methyl o-Trifluoromethylbenzoylacetate

Yield: 397 mg, Recovery: 78.8%; $^1$H-NMR (500 MHz, CDCl$_3$) of the ester compound represented by the following structural formula:

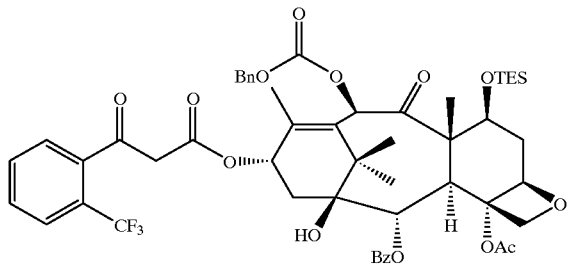

σ(ppm); 12.37 (0.70H, s), 8.05–8.12 (2H, m), 7.78 (1H, d, J=7.3 Hz), 7.55–7.78 (4H, m), 7.30–7.51 (7H, m), 6.30 (0.70H, s), 6.28 (0.30H, s), 6.18–6.27 (1H, m), 5.65–5.71 (1H, m), 5.41 (0.70H, s), 5.24, 5.17 (0.70H*2, ABq, J=12.2 Hz), 5.23, 5.16 (0.30H*2, ABq, J=12.2 Hz), 4.94 (1H, bd, J=9.5 Hz), 4.47 (1H, dd, J=10.4, 6.7 Hz), 4.30 (1H, bd, J=8.5 Hz), 4.18 (1H, bd, J=8.5 Hz), 4.10, 3.98 (0.30H*2, ABq, J=15.9 Hz), 3.77–3.85 (1H, m), 2.48–2.57 (1H, m), 2.35–2.44 (0.70H, m), 2.28 (0.30H*3, s), 2.27 (0.70H*3, s), 2.24–2.32 (0.70H+0.30H*2, m), 2.10–2.13 (0.70H*3, m), 2.05–2.08 (0.30H*3, m), 1.86–1.93 (1H, m), 1.70 (0.70H*3, s), 1.69 (0.30H*3, s), 1.23 (0.70H*3, bs), 1.20 (0.7H*3+ 0.3H*3, s), 1.16 (0.30H*3, s), 0.87–0.96 (9H, m), 0.52–0.63 (6H, m).

Example 16

Methyl m-Trifluoromethylbenzoylacetate

Yield: 284 mg, Recovery: 56.3%; $^1$H-NMR (500 MHz, CDCl$_3$) of the ester compound represented by the following structural formula:

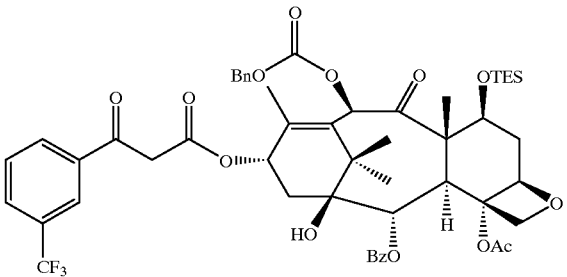

σ(ppm); 12.50 (0.55H, s), 8.24 (0.45H, bs), 8.18 (0.45H, bd, J=8.0 Hz), 8.05–8.12 (2H, m), 8.05 (0.55H, bs), 7.98 (0.55H, bd, J=8.0 Hz), 7.92 (0.45H, bd, J=7.9 Hz), 7.79 (0.55H, bd, J=8.0 Hz), 7.70 (0.45H, t, J=7.9 Hz), 7.56–7.65 (1H+0.55H, m), 7.30–7.51 (7H, m), 6.32 (0.55H, s), 6.27 (0.45H, s), 6.19–6.30 (1H, m), 5.78 (0.55H, s), 5.65–5.71 (1H, m), 5.24, 5.17 (0.55H*2, ABq, J=12.3 Hz), 5.23, 5.16 (0.45H*2, ABq, J=12.0 Hz), 4.97 (0.55H, bd, J=8.3 Hz), 4.92 (0.45H, bd, J=8.0 Hz), 4.50 (0.55H, dd, J=10.4, 6.7 Hz), 4.45 (0.45H, dd, J=10.4, 6.7 Hz), 4.28–4.35 (1H, m), 4.19, 4.13 (0.55H*2, ABq, J=15.4 Hz), 4.13–4.19 (1H, m), 3.84 (0.55H, d, J=7.0 Hz), 3.79 (0.45H, d, J=7.1 Hz), 2.48–2.60 (1H, m), 2.35–2.44 (1H, m), 2.36 (0.55H*3, s), 2.23–2.32 (1H, m), 2.27 (0.45H*3, s), 2.15 (0.55H*3, d, J=1.2 Hz), 2.03 (0.45H*3, d, J=1.2 Hz), 1.86–1.94 (1H, m), 1.71 (0.55H*3, s), 1.69 (0.45H*3, s), 1.23 (0.45H*3, s), 1.21 (0.45H*3, s), 1.20 (0.55H*3, s), 1.17 (0.55H*3, s), 0.88–0.94 (9H, m), 0.53–0.61 (6H, m).

Example 17

Methyl p-Trifluoromethylbenzoylacetate

Yield: 362 mg, Recovery: 71.8%; $^1$H-NMR (500 MHz, CDCl$_3$) of the ester compound represented by the following structural formula:

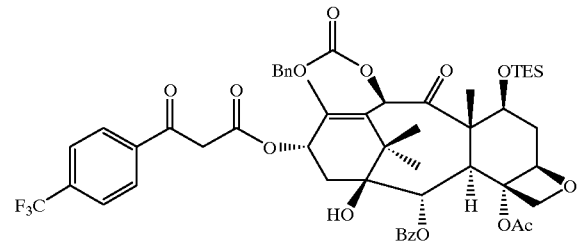

σ(ppm); 12.51 (0.60H, s), 8.11 (0.40H*2, d, J=8.2 Hz), 8.05–8.10 (2H, m), 7.92 (0.60H*2, d, J=8.8 Hz), 7.81 (0.40H*2, d, J=8.2 Hz), 7.73 (0.60H*2, d, J=8.8 Hz), 7.57–7.64 (1H, m), 7.32–7.52 (7H, m), 6.32 (0.60H, s), 6.27 (0.40H, s), 6.20–6.30 (1H, m), 5.79 (0.60H, s), 5.65–5.71 (1H, m), 5.24, 5.17 (0.60H*2, ABq, J=12.3 Hz), 5.22, 5.16 (0.40H*2, ABq, J=12.1 Hz), 4.97 (0.60H, bd, J=8.3 Hz), 4.93 (0.40H, bd, J=8.0 Hz), 4.50 (0.60H, dd, J=10.6, 6.9 Hz), 4.45 (0.40H, dd, J=10.4, 6.7 Hz), 4.29–4.34 (1H, m), 4.18, 4.13 (0.4H*2, ABq, J=15.6 Hz), 4.12–4.20 (1H, m), 3.84 (0.60H, d, J=6.7 Hz), 3.79 (0.40H, d, J=7.0 Hz), 2.48–2.59 (1H, m), 2.23–2.44 (2H, m), 2.36 (0.60H*3, s), 2.26 (0.40H*3, s), 2.15 (0.60H*3, bd, J=1.2 Hz), 2.03 (0.40H*3, bd, J=1.2 Hz), 1.86–1.95 (1H, m), 1.71 (0.60H*3, s), 1.69 (0.40H*3, s), 1.22 (0.60H*3, s), 1.204 (0.40H*3, s), 1.200 (0.60H*3, s), 1.17 (0.40H*3, s), 0.87–0.95 (9H, m), 0.53–0.61 (6H, m).

Example 18

Methyl m-Fluorobenzoylacetate

Yield: 367 mg, Recovery: 76.6%; $^1$H-NMR (500 MHz, CDCl$_3$) of the ester compound represented by the following structural formula:

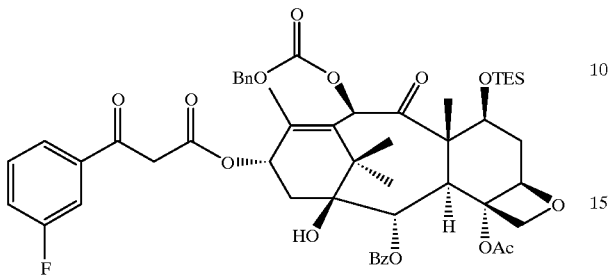

σ(ppm); 12.49 (0.50H, s), 8.03–8.12 (2H, m), 7.74–7.79 (0.50H, m), 7.66–7.72 (0.50H, m), 7.30–7.64 (11H, m), 6.32 (0.50H, s), 6.27 (0.50H, s), 6.19–6.30 (1H, m), 5.73 (0.50H, s), 5.63–5.71 (1H, m), 5.24, 5.17 (0.50H*2, ABq, J=12.2 Hz), 5.23, 5.16 (0.50H*2, ABq, J=12.1 Hz), 4.97 (0.50H, bd, J=8.0 Hz), 4.92 (0.50H, bd, J=7.9 Hz), 4.50 (0.50H, dd, J=10.6, 6.6 Hz), 4.45 (0.50H, dd, J=10.4, 6.7 Hz), 4.27–4.34 (1H, m), 4.08–4.20 (3H, m), 3.84 (0.50H, d, J=6.7 Hz), 3.79 (0.50H, d, J=6.7 Hz), 2.48–2.59 (1H, m), 2.20–2.43 (2H, m), 2.36 (0.50H*3, s), 2.25 (0.50H*3, s), 2.14 (0.50H*3, d, J=1.3 Hz), 2.02 (0.50H*3, d, J=1.4 Hz), 1.86–1.94 (1H, m), 1.79 (0.50H*3, s), 1.69 (0.50H*3, s), 1.22 (0.50H*3, s), 1.20 (0.50H*3, s), 1.19 (0.50H*3, s), 1.18 (0.50H*3, s), 0.86–0.95 (9H, m), 0.52–0.63 (6H, m).

Example 19

Methyl 2-Furanoyl acetate

Yield: 224 mg, Recovery: 48.2%; $^1$H-NMR (500 MHz, CDCl$_3$) of the ester compound represented by the following structural formula:

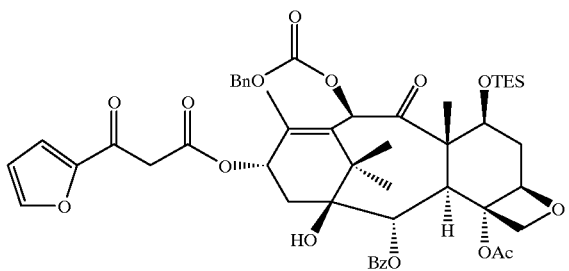

σ(ppm); 12.03 (0.15H, s), 8.03–8.12 (2H, m), 7.13–7.68 (12H, m), 6.62 (0.85H, dd, J=3.7, 1.9 Hz), 6.56 (0.15H, dd, J=3.6, 1.8 Hz), 6.31 (0.15H, s), 6.27 (0.85H, s), 6.18–6.30 (1H, m), 5.71 (0.15H, s), 5.65–5.70 (1H, m), 5.23, 5.16 (0.15H*2, ABq, J=12.2 Hz), 5.22, 5.15 (0.85H*2, ABq, J=12.1 Hz), 4.98 (0.85H, dd, J=10.4, 6.7 Hz), 4.97 (0.15H, bd, J=9.8 Hz), 4.93 (0.85H, bd, J=8.3 Hz), 4.84 (0.15H, d, J=7.0 Hz), 4.80 (0.85H, d, J=7.0 Hz), 4.50 (0.15H, dd, J=10.4, 6.4 Hz), 4.27–4.35 (1H, m), 4.13–4.20 (1H, m), 4.04, 3.94 (0.85H*2, ABq, J=15.5 Hz), 2.47–2.57 (1H, m), 2.37 (0.15H*3, s), 2.29 (0.85H*3, s), 2.20–2.40 (2H, m), 2.12 (0.15H*3, bs), 2.04 (0.85H*3, bs), 1.85–1.93 (1H, m), 1.72 (0.15H*3, bs), 1.71 (0.85H*3, bs), 1.23 (0.15H*3, s), 1.22 (0.85H*3, s), 1.20 (0.15H*3, s), 1.19 (0.85H*3, s), 0.88–0.95 (9H, m), 0.52–0.62 (6H, m).

Example 20

Methyl Cyclohexanoylacetate

Yield: 279 mg, Recovery: 59.0%; $^1$H-NMR (500 MHz, CDCl$_3$) of the ester compound represented by the following structural formula:

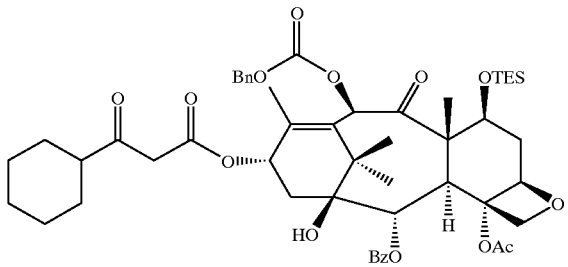

σ(ppm); 12.06 (0.4H, s), 8.03–8.12 (2H, m), 7.57–7.63 (1H, m), 7.43–7.51 (2H, m), 7.31–7.43 (5H, m), 6.30 (0.4H, s), 6.28 (0.6H, s), 6.22 (0.6H, bt, J=8.4 Hz), 6.14 (0.4H, bt, J=8.6 Hz), 5.66 (1H, d, J=7.0 Hz), 5.16, 5.23 (2H, ABq, J=12.2 Hz), 5.05 (0.4H, s), 4.90–4.99 (1H, m), 4.42–4.51 (1H, m), 4.26–4.33 (1H, m), 4.16 (1H, d, J=8.5 Hz), 3.81 (0.4H, d, J=7.4 Hz), 3.78 (0.6H, d, J=7.0 Hz), 3.56, 3.66 (0.6H*2, ABq, J=15.5 Hz), 2.66 (0.6H*3, bs), 2.48–2.57 (2H, m), 2.32 (0.4H*3, s), 2.26 (0.6H*3, s), 2.15–2.35 (2H, m), 2.09 (0.4H*3, bs), 1.78–1.95 (5H, m), 1.70 (0.4H*3, s), 1.69 (0.6H*3, s), 1.59–1.74 (3H, m), 1.25–1.43 (3H, m), 1.20 (3H, bs), 1.17 (3H, bs), 0.87–0.95 (9H, m), 0.53–0.62 (6H, m).

Examples 21 to 23

In Examples 14 to 20, the reactions were conducted in the presence of a solvent, but in Examples 21 to 23, baccatin derivatives were prepared in the absence of the solvent. Hereinafter, yield etc. are shown when various β-ketoesters were used.

β-ketoesters (20 equivalents relative to Compound (3)) and 12 mg (or 37 mg in Example 23) of 4-dimethylaminopyridine (DMAP) were added to 79 mg (or 396 mg in Example 23) of Compound (3) in Example 1, and the mixture was reacted at 90° C. under reduced pressure for 1.5 hours (or, for 4 hours in Example 23) whereby various baccatin derivatives were obtained. The yield, $^1$H-NMR etc. are described below.

Example 21

Methyl p-Methoxybenzoylacetate

Yield: 103 mg, Recovery: quantitative.

The product was the ester compound represented by the following structural formula, and its $^1$H-NMR (500 MHz, CDCl$_3$) is as shown in Example 14.

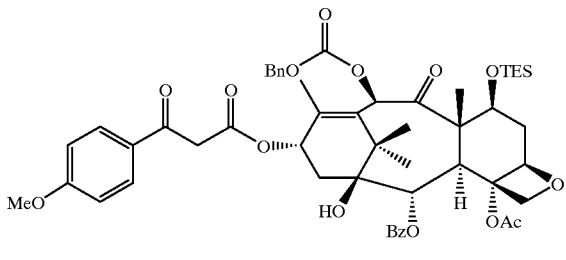

Example 22

Methyl o-Fluorobenzoylacetate

Yield: 91 mg, Recovery: 94.8%; ¹H-NMR (500 MHz, CDCl₃) of the ester compound represented by the following structural formula:

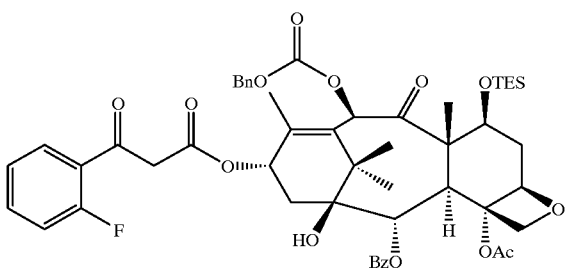

σ(ppm); 12.56 (0.45H, s), 8.18–8.22 (0.45H, m), 8.03–8.12 (0.55H*2+0.45H, m), 7.92–8.01 (1H, m), 7.14–7.70 (11H, m), 6.31 (0.45H, s), 6.29 (0.55H, s), 6.20–6.29 (1H, m), 6.00 (0.45H, s), 5.68 (0.45H, d, J=6.9 Hz), 5.67 (0.55H, d, J=6.9 Hz), 5.17, 5.242 (0.45H*2, ABq, J=12.2 Hz), 5.16, 5.236 (0.55H*2, ABq, J=12.2 Hz), 4.96 (0.45H, bd, J=8.2 Hz), 4.93 (0.55H, bd, J=8.6 Hz), 4.50 (0.45H, dd, J=10.4, 6.7 Hz), 4.47 (0.55H, dd, J=10.7, 6.8 Hz), 4.28–4.33 (1H, m), 4.13–4.20 (1H+0.55H, m), 4.09 (0.55H, dd (AB), J=16.6, 3.5 Hz), 3.85 (0.45H, d, J=7.0 Hz), 3.81 (0.55H, d, J=7.0 Hz), 2.48–2.58 (1H, m), 2.38 (0.45H*3, s), 2.26 (0.55H*3, s), 2.23–2.40 (2H, m), 2.13 (0.45H*3, bs), 2.09 (0.55H*3, bs), 1.86–1.93 (1H, m), 1.71 (0.45H*3, s), 1.70 (0.55H*3, s), 1.22 (0.45H*3, s), 1.20 (0.55H*3, s), 1.19 (0.45H*3, s), 1.17 (0.55H*3, s), 0.91 (9H, t, J=15.9 Hz), 0.52–0.62 (6H, m).

Example 23

Methyl Cyclopropanoylacetate

Yield: 400 mg, Recovery: 88.6%; ¹H-NMR (500 MHz, CDCl₃) of the ester compound represented by the following structural formula:

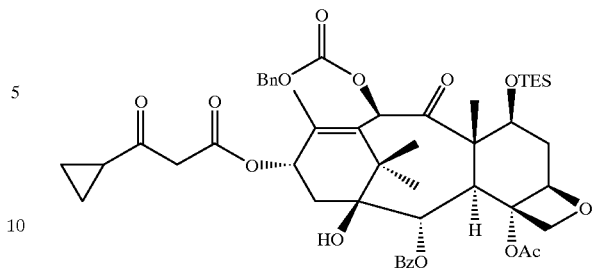

σ(ppm); 12.18 (0.05H, s), 8.04–8.10 (2H, m), 7.58–7.64 (1H, m), 7.45–7.52 (2H, m), 7.31–7.43 (5H, m), 6.30 (0.05H, s), 6.28 (0.95H, s), 6.20–6.28 (0.95H, m), 6.11–6.17 (0.05H, m), 5.66 (1H, d, J=7.0 Hz), 5.16, 5.23 (1H*2, ABq, J=12.2 Hz), 4.94 (1H, bd, J=8.2 Hz), 4.46 (1H, dd, J=6.7, 9.7 Hz), 4.30 (1H, d, J=8.5 Hz), 4.15 (1H, d, J=8.5 Hz), 3.79 (1H, d, J=7.0 Hz), 3.74, 3.69 (1H*2, ABq, J=15.0 Hz), 2.52 (1H, ddd, J=6.7, 9.5, 14.4 Hz), 2.22–2.37 (2H, m), 2.29 (3H, s), 2.05–2.12 (1H, m), 2.08 (3H, s), 1.85–1.93 (1H, m), 1.70 (3H, s), 1.15–1.23 (2H, m), 1.20 (3H, s), 1.17 (3H, s), 1.00–1.08 (2H, m), 0.87–0.96 (9H, m), 0.53–0.63 (6H, m).

Example 24

Production of 7-Triethylsilyl-10-benzyloxycarbonyl-13-(3-phenyl-3-keto-propanoyl)-10-deacetyl-baccatin III 0.343 ml of ethyl benzoylacetate was added to 79 mg of compound (Compound (3), C₄₃H₅₆O₁₂Si, a molecular weight of 792.99), that is, 10-deacetylbaccatin III (1) wherein a hydroxyl group at the 7-position was protected with a triethylsilyl group and a hydroxyl group at the 10-position was protected with a benzyloxycarbonyl group according to the conventional method, and the mixture was reacted at 90° C. under reduced pressure (0.5 mmHg) for 3 hours, and this solution was purified by a silica gel column to give 85 mg of ester compound (Compound (4), C₅₂H₆₂O₁₄Si, a molecular weight of 939.14).

This compound was dissolved in chloroform-d and analyzed by ¹H-NMR, and its structure was determined by assignment of each peak, and it was thus confirmed that the product is represented by the structural formula shown as Compound (4) in the reaction scheme II. The ¹H-NMR of this compound was identical with that of the compound obtained in Example 1.

Example 25

The reaction was conducted in the same manner as in Example 24 except that the reaction temperature was 70° C.

0.343 ml of ethyl benzoylacetate was added to 79 mg of Compound (3) in Example 24, and the mixture was reacted at 70° C. under reduced pressure (0.5 mmHg) for 27 hours, and excess ethyl benzoylacetate was distilled away in a Kugel Rohr distillation device.

The residue was purified by a silica gel column to give 85 mg of ester compound (Compound (4), C₅₂H₆₂O₁₄Si, a molecular weight of 939.14). ¹H-NMR also indicated that this compound is identical with the compound obtained in Example 24.

Example 26

The reaction was conducted in the same manner as in Example 24 except that the reaction temperature was 50° C.

0.343 ml of ethyl benzoylacetate was added to 79 mg of Compound (3) in Example 24, and the mixture was reacted at 50° C. under reduced pressure (0.5 mmHg) for 21 hours, and this solution was purified by a silica gel column to give 8 mg of ester compound (Compound (4), $C_{52}H_{62}O_{14}Si$, a molecular weight of 939.14). $^1$H-NMR analysis also indicated that this compound is identical with the compound obtained in Example 24. The starting material was also recovered by 71 mg.

Example 27

The reaction was conducted in the same manner as in Example 24 except that the pressure during the reaction was atmospheric pressure (760 mmHg).

0.343 ml of ethyl benzoylacetate was added to 79 mg of Compound (3) in Example 24 and allowed to react at 90° C. at atmospheric pressure for 24 hours, and the solution was purified by a silica gel column to give 77 mg of ester compound (Compound (4), $C_{52}H_{62}O_{14}Si$, a molecular weight of 939.14). $^1$H-NMR analysis also indicated that this compound is identical with the compound obtained in Example 24.

Example 28

The reaction was conducted in the same manner as in Example 24 except that the pressure during the reaction was reduced pressure (20 mmHg) and the amount of ethyl benzoylacetate was reduced.

0.086 ml of ethyl benzoylacetate was added to 79 mg of Compound (3) in Example 24 and allowed to react at 90° C. under reduced pressure (20 mmHg) for 10 hours, and excess ethyl benzoylacetate was distilled away in a Kugel Rohr distillation device.

The residue was purified by a silica gel column to give 88 mg of ester compound (Compound (4), $C_{52}H_{62}O_{14}Si$, a molecular weight of 939.14). $^1$H-NMR analysis also indicated that this compound is identical with the compound obtained in Example 24.

Example 29

The reaction was conducted in the same manner as in Example 24 except that the pressure during the reaction was reduced pressure (20 mmHg) and the amount of ethyl benzoylacetate was reduced.

0.034 ml of ethyl benzoylacetate was added to 79 mg of Compound (3) in Example 24 and allowed to react at 90° C. under reduced pressure (20 mmHg) for 24 hours, and this solution was purified by a silica gel column to give 40 mg of ester compound (Compound (4), $C_{52}H_{62}O_{14}Si$, a molecular weight of 939.14). $^1$H-NMR analysis also indicated that this compound is identical with the compound obtained in Example 24. Further, the starting material was recovered by 43 mg.

Example 30

The reaction in Example 24 was conducted in the absence of a solvent, but in this example, the reaction was conducted using triethylene glycol dimethyl ether as the solvent.

0.086 ml of ethyl benzoylacetate and 0.2 ml of triethylene glycol dimethyl ether were added to 79 mg of Compound (3) in Example 24 and allowed to react at 90° C. under reduced pressure (20 mmHg) for 24 hours, and this solution was purified by a silica gel column to give 87 mg of ester compound (Compound (4), $C_{52}H_{62}O_{14}Si$, a molecular weight of 939.14). $^1$H-NMR analysis also indicated that this compound is identical with the compound obtained in Example 24.

Example 31

The reaction was conducted in the same manner as in Example 30 except that the amount of ethyl benzoylacetate was reduced.

0.034 ml of ethyl benzoylacetate and 0.2 ml of triethylene glycol dimethyl ether were added to 79 mg of Compound (3) in Example 24 and allowed to react at 90° C. under reduced pressure (20 mmHg) for 20 hours, and this solution was purified by a silica gel column to give 61 mg of ester compound (Compound (4), $C_{52}H_{62}O_{14}Si$, a molecular weight of 939.14). $^1$H-NMR analysis also indicated that this compound is identical with the compound obtained in Example 24. Further, the starting material was recovered by 27 mg.

Examples 32 and 33

In Example 24, the 10-position in the baccatin was a benzyloxycarbonyl group, but in these examples it is shown that the same reaction can be conducted even if the group at the 10-position is an acetyl group or an allyloxycarbonyl group.

0.343 ml of ethyl benzoylacetate was added to the baccatin (0.1 mmol) protected at the 7-position with a triethylsilyl group and at the 10-position with an acetyl group or an allyloxycarbonyl group, and the mixture was reacted at 90° C. under reduced pressure (0.5 mmHg) for 3 hours, and excess ethyl benzoylacetate was distilled away in a Kugel Rohr distillation device.

The residue was purified by a silica gel column to give the ester compound. The measurement results of yield, $^1$H-NMR etc. are described below.

Example 32

Baccatin Wherein a Protecting Group at the 10-Position is an Acetyl Group is used Yield: 77 mg, Recovery: 91%.

The product is the ester compound represented by the following structural formula, and its $^1$H-NMR (500 MHz, $CDCl_3$) is the same as that of the compound in Example 4.

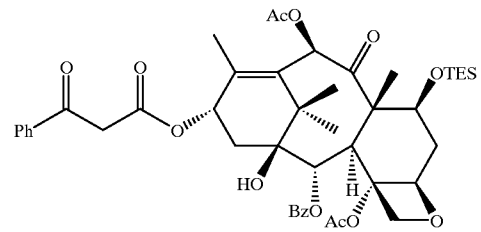

Example 33

Baccatin Wherein a Protecting Group at the 10-Position is an Allyloxycarbonyl Group is used Yield: 85 mg, Recovery: 96%.

The product is the ester compound represented by the following structural formula, and its $^1$H-NMR (500 MHz, $CDCl_3$) is the same as that of the compound in Example 5.

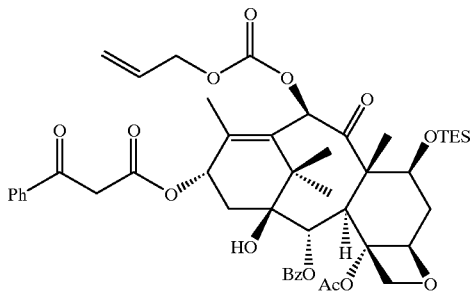

Examples 34 to 42

As the β-ketoester, various β-ketoesters other than ethyl benzoylacetate can be used to produce the desired compound. Hereinafter, yield etc. when various β-ketoesters were used are described.

β-ketoesters (10 or 20 equivalents relative to Compound (3)) were added to 79 mg of Compound (3) in Example 24 and allowed to react at 90° C. under reduced pressure (20 mmHg) to give various baccatin derivatives. The amount of β-ketoesters, reaction time, yield, ¹H-NMR etc. are as follows.

Example 34

Methyl p-Methoxybenzoylacetate

β-ketoester: 10 equivalents, reaction time: 7 hours, yield: 96 mg, recovery: 99%.

The product is the ester compound represented by the following structural formula, and its ¹H-NMR (500 MHz, CDCl₃) is the same as that of the compound in Example 14.

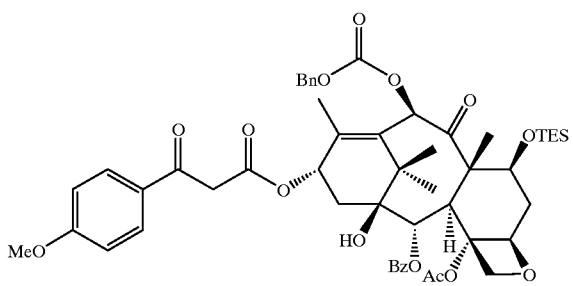

Example 35

Methyl m-Fluorobenzoylacetate β-ketoester: 10 equivalents, reaction time: 6 hours, yield: 84 mg, recovery: 88%.

The product is the ester compound represented by the following structural formula, and its ¹H-NMR (500 MHz, CDCl₃) is the same as that of the compound in Example 18.

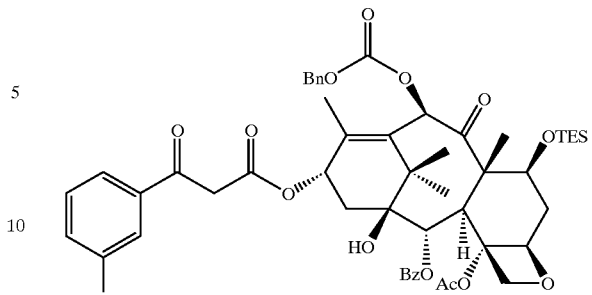

Example 36

Methyl o-Fluorobenzoylacetate

β-ketoester: 10 equivalents, reaction time: 6 hours, yield: 88 mg, recovery: 92%.

The product is the ester compound represented by the following structural formula, and its ¹H-NMR (500 MHz, CDCl₃) is the same as that of the compound in Example 22.

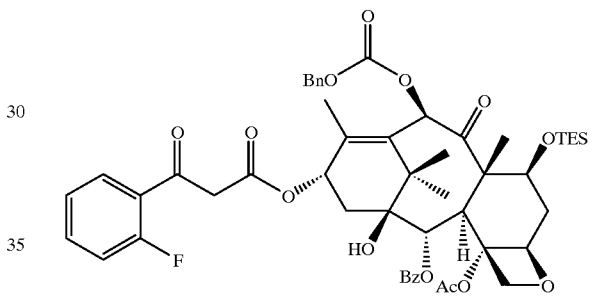

Example 37

Methyl p-Fluorobenzoylacetate

β-ketoester: 10 equivalents, reaction time: 6 hours, yield: 90 mg, recovery: 94%.

¹H-NMR (500 MHz, CDCl₃) of the ester compound represented by the following structural formula:

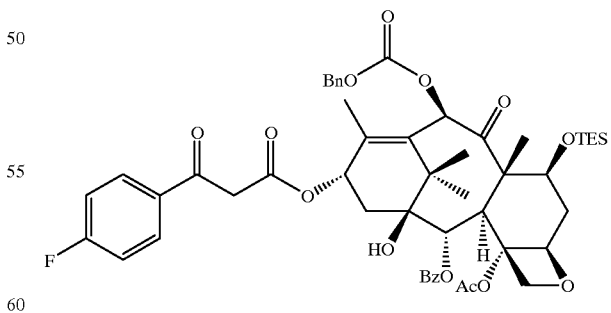

σ(ppm); 7.10–8.13 (m, 14H), 6.14–6.35 (m, 2H), 5.60–5.74 (m, 1H), 5.10–5.30 (m, 2H), 4.88–5.04 (m, 1H), 4.40–4.55 (m, 1H), 4.26–4.35 (m, 1H), 4.05–4.22 (m, 3H), 3.74–3.91 (m, 1H), 2.48–2.60 (m, 1H), 2.22–2.44 (m, 5H), 1.97–2.18 (m, 3H), 1.84–1.96 (m, 1H), 1.65–1.74 (m, 3H), 1.15–1.24 (m, 6H), 0.82–0.98 (m, 9H), 0.50–0.64 (m, 6H).

Example 38

Methyl m-Trifluoromethylbenzoylacetate

Yield: 284 mg, Recovery: 56.3%.

The product is the ester compound represented by the following structural formula, and its ¹H-NMR (500 MHz, CDCl₃) is the same as that of the compound in Example 16.

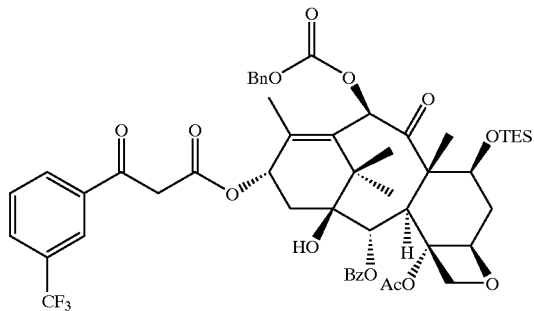

Example 39

Methyl 2-Furanoylacetate

β-ketoester: 20 equivalents, reaction time: 8 hours. Yield: 61 mg, recovery: 66%.

The product is the ester compound represented by the following structural formula, and its ¹H-NMR (500 MHz, CDCl₃) is the same as that of the compound in Example 19.

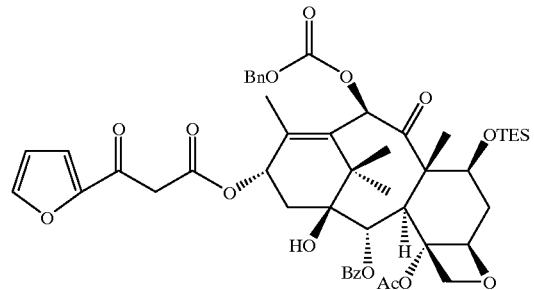

Example 40

Methyl Cyclohexanoylacetate

β-ketoester: 10 equivalents, reaction time: 6 hours, Yield: 90 mg, recovery: 95%.

The product is the ester compound represented by the following structural formula, and its ¹H-NMR (500 MHz, CDCl₃) is the same as that of the compound in Example 20.

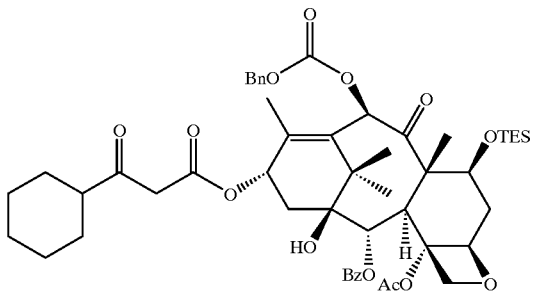

Example 41

Methyl Cyclopropanoylacetate

β-ketoester: 10 equivalents, reaction time: 6 hours, Yield: 85 mg, recovery: 94%.

The product is the ester compound represented by the following structural formula, and its ¹H-NMR (500 MHz, CDCl₃) is the same as that of the compound in Example 23.

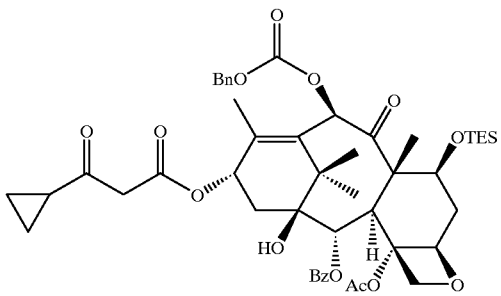

Example 42

Methyl 2-Oxocyclopentylacetate

β-ketoester: 20 equivalents, reaction time: 5 hours, Yield: 84 mg, recovery: 93%.

¹H-NMR (500 MHz, CDCl₃) of the ester compound represented by the following structural formula:

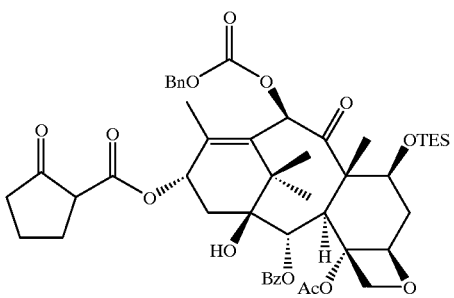

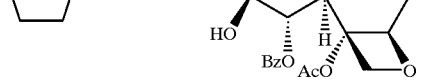

σ(ppm); 0.53–0.60(m, 6H, TES), 0.86–0.93(m, 9H, TES), 1.17(s), 1.21(s), 1.56(s), 1.69(s), 1.70(s), 2.05(s), 1.86–1.98 (m, 2H), 2.12–2.58(m, 8H), 3.22(t, J=7.6 Hz, 2'-H), 3.24(t, J=8.8 Hz, 2'-H), 3.80(d, J=6.7 Hz, 3-H), 3.81(d, J=5.5 Hz, 3-H), 4.17(d, J=8.8 Hz, 20-H), 4.30(d, J=8.6 Hz, 20-H), 4.45(dd, J=6.8, 10.4 Hz, 7-H), 4.49(dd, J=6.7, 10.7 Hz, 7-H), 4.95(m, 1H, 5-H), 5.16(d, J=12.2 Hz, Bn), 5.23(d, J=12.2 Hz, Bn), 5.67(d, J=7.0 Hz, 1H, 2-H), 6.16(t, J=8.3 Hz, 13-H), 6.24(t, J=9.0 Hz, 13-H), 6.27(s, 10-H), 6.31(s, 10-H), 7.16–7.26(m, 1H), 7.32–7.42(m, 4H), 7.45–7.52(m, 2H), 7.57–7.64(m, 1H), 8.06–8.11(m, 2H).

Example 43

In Examples 34 to 42, the condition of reduced pressure was 20 mmHg, but in Example 43, the reaction was conducted at a pressure of 1 mmHg.

384 mg of methyl 2-methylbenzoylacetate was added to 79 mg of Compound (3) in Example 24, and the mixture was reacted at 90° C. under reduced pressure (1 mmHg) for 25 hours, and the reaction solution was poured into 1 N aqueous hydrochloric acid and extracted with ethyl acetate. The organic phase was washed with aqueous saturated sodium hydrogencarbonate, concentrated and purified by a silica gel column to give 19 mg of ester compound ($C_{53}H_{64}O_{14}Si$, a molecular weight of 953.17).

This compound was dissolved in chloroform-d and analyzed by $^1$H-NMR, and its structure was determined by assignment of each peak, and it was thus confirmed that the product was represented by the following structural formula.

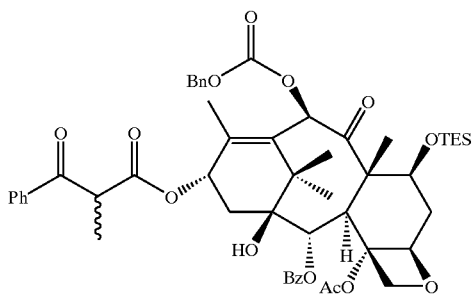

σ(ppm); 0.48–0.64(m, 6H), 0.78–0.99 (m, 9H), 1.08–1.37 (m, 9H), 1.50–2.44 (m, 12H), 2.44–2.60 (m, 1H), 3.69–3.91 (m, 1H), 4.07–4.19 (m, 2H), 4.23–4.35 (m, 1H), 4.37–4.53 (m, 1H), 4.86–5.03 (m, 1H), 5.10–5.29 (m, 2H), 5.61–5.76 (m, 1H), 6.14–6.46 (m, 2H), 7.12–7.68 (m, 11H), 7.77–8.14 (m, 4H).

What is claimed is:

1. A baccatin derivative represented by the general formula (I):

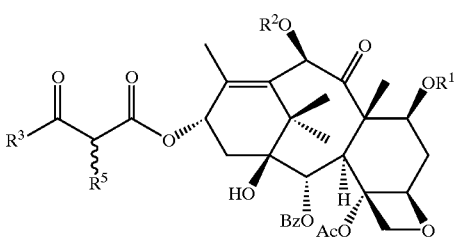

(I)

(wherein $R^1$ and $R^2$ simultaneously or independently represent a hydroxyl-protecting group, $R^3$ represents any one group selected from the group of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group and a thienyl group, $R^5$ represents a hydrogen atom or an alkyl group, Bz represents a benzoyl group, and Ac represents an acetyl group).

2. A process for producing a baccatin derivative represented by the general formula (I) described in claim 1, which comprises allowing a baccatin represented by the general formula (II):

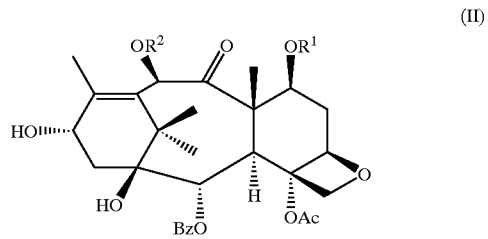

(II)

(wherein $R^1$ and $R^2$ simultaneously or independently represent a hydroxyl-protecting group, Bz represents a benzoyl group, and Ac represents an acetyl group), to react with a β-ketoester in the presence of a tin compound or an amine base.

3. The process according to claim 2, wherein the reaction is conducted under reduced pressure.

4. A process for producing a baccatin derivative represented by the general formula (I) in claim 1, which comprises allowing a baccatin represented by the general formula (II):

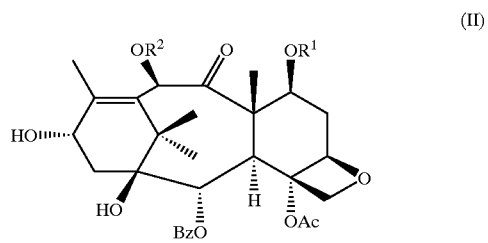

(II)

(wherein $R^1$ and $R^2$ simultaneously or independently represent a hydroxyl-protecting group, Bz represents a benzoyl group, and Ac represents an acetyl group), to react with a β-ketoester in the absence of a catalyst.

5. The process according to claim 4, wherein the reaction is conducted under reduced pressure.

6. A baccatin derivative represented by the general formula (III):

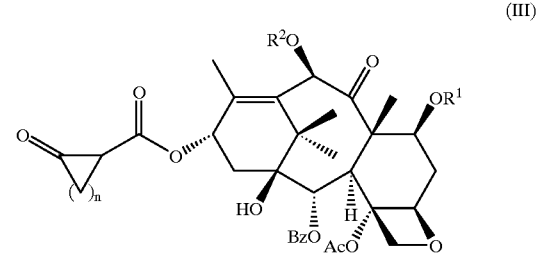

(III)

(wherein $R^1$ and $R^2$ simultaneously or independently represent a hydroxyl-protecting group, n is an integer of 1 to 5, Bz represents a benzoyl group, and Ac represents an acetyl group).

7. A method of producing paclitaxel, comprising;
  (a) deprotecting the hydroxyl group at C-7 of a baccatin derivative as claimed in claim 1; and
  (b) converting the C-10 and C-13 hydroxyl substituents of the baccatin derivative of formula (I) to the C-10 and C-13 substituents of paclitaxel.

8. A baccatin derivative represented by the formula (I) described in claim 1, wherein $R^1$ and $R^2$ are protecting groups taken from the group consisting of a triethylsilyl group, a benzyloxycarbonyl group, an acetyl group, and allyloxycarbonyl group.

9. A baccatin derivative represented by the formula (III) described in claim 6, wherein $R^1$ and $R^2$ are protecting groups taken from the group consisting of a triethylsilyl group, a benzyloxycarbonyl group, an acetyl group, and allyloxycarbonyl group.

10. The process according to claim 2, wherein the β-ketoester represented by the formula:

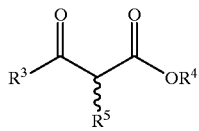

wherein $R^3$ is an unsubstituted or a substituted phenyl group, an unsubstituted or a substituted furyl group, an unsubstituted or a substituted pyridinyl group, an alkyl group, a hydroxyalkyl group, a halogenated alkyl group, a cyclic alkyl group, or a thienyl group, $R^4$ is the nucleus of an alcohol, and $R^5$ is a hydrogen atom or an alkyl group.

11. The process according to claim 10, wherein $R^3$ is a phenyl group, a p-methoxyphenyl group, a 2-furyl group, an o-trifluoro-methylphenyl group, a m-fluorophenyl group, or a cyclohexyl group.

12. The process according to claim 10, wherein $R^4$ is a methyl group, an ethyl group, an isopropyl group, or an alkyl group.

13. The process according to claim 4, wherein the β-ketoester represented by the formula:

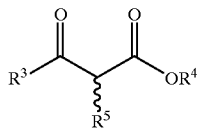

wherein $R^3$ is an unsubstituted or a substituted phenyl group, an unsubstituted or a substituted furyl group, an unsubstituted or a substituted pyridinyl group, an alkyl group, a hydroxyalkyl group, a halogenated alkyl group, a cyclic alkyl group, or a thienyl group, $R^4$ is the nucleus of an alcohol, and $R^5$ is a hydrogen atom or an alkyl group.

14. The process according to claim 13, wherein $R^3$ is a phenyl group, a p-methoxyphenyl group, a 2-furyl group, an o-trifluoro-methylphenyl group, a m-fluorophenyl group, or a cyclohexyl group.

15. The process according to claim 13, wherein $R^4$ is a methyl group, an ethyl group, an isopropyl group, or an alkyl group.

16. The process according to claim 2, wherein the β-ketoester represented by the formula:

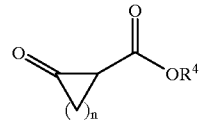

wherein n is an integer from 1 to 5.

17. The process according to claim 4, wherein the β-ketoester represented by the formula:

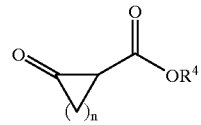

wherein n is an integer from 1 to 5.

18. The process according to claim 2, wherein the β-ketoester is selected from the group consisting of methyl p-methoxybenzoylacetate, methyl o-trifluoromethylbenzoylacetate, methyl m-trifluoromethylbenzoylacetate, methyl p-trifluoromethylbenzoyl-acetate, methyl o-fluorobenzoylacetate, methyl m-fluorobenzoylacetate, methyl 2-furanoyl-acetate, methyl cyclohexanoylacetate, methyl 2-oxocyclopentylacetate, and methyl 2-methylbenzoylacetate.

19. The process according to claim 4, wherein the β-ketoester is selected from the group consisting of methyl p-methoxybenzoylacetate, methyl o-trifluoromethyl benzoylacetate, methyl m-trifluoromethylbenzoylacetate, methyl p-trifluoromethylbenzoyl acetate, methyl o-fluorobenzoylacetate, methyl m-fluorobenzoylacetate, methyl 2-furanoyl-acetate, methyl cyclohexanoylacetate, methyl 2-oxocyclopentylacetate, and methyl 2-methylbenzoylacetate.

20. The process according to claim 2, wherein the tin compound is 1-chloro-3-hydroxy-tetrabutyldistannoxane or 1,3-dichlorotetrabutyldistannoxane.

* * * * *